United States Patent
Günther

(10) Patent No.: US 7,735,765 B2
(45) Date of Patent: Jun. 15, 2010

(54) ROTATION TRANSFORMER FOR CABLE CONNECTIONS

(75) Inventor: Wolfgang Günther, Penig/Tauscha (DE)

(73) Assignee: Conductix-Wampfler AG, Weil am Rhein-Markt (DE)

( * ) Notice: Subject to any disclaimer, the term of this patent is extended or adjusted under 35 U.S.C. 154(b) by 167 days.

(21) Appl. No.: 11/568,912

(22) PCT Filed: Apr. 15, 2005

(86) PCT No.: PCT/EP2005/003967

§ 371 (c)(1),
(2), (4) Date: Jan. 10, 2007

(87) PCT Pub. No.: WO2005/112215

PCT Pub. Date: Nov. 24, 2005

(65) Prior Publication Data
US 2007/0228205 A1   Oct. 4, 2007

(30) Foreign Application Priority Data
May 11, 2004   (DE) .................. 20 2004 007 741 U

(51) Int. Cl.
*B65H 75/38* (2006.01)
*B65H 75/44* (2006.01)
*B65H 23/04* (2006.01)

(52) U.S. Cl. .................... 242/388.6; 242/602; 242/603; 242/615.3; 242/407

(58) Field of Classification Search ................ 242/407, 242/388.6, 388.91, 603, 608.1, 614, 602, 242/615.3, 615.4; *H02G 11/02; B65H 75/44*
See application file for complete search history.

(56) References Cited

U.S. PATENT DOCUMENTS

| | | | | |
|---|---|---|---|---|
| 2,432,270 A * | 12/1947 | Asbill, Jr. | ................ | 242/118.4 |
| 2,728,530 A * | 12/1955 | Goldberg et al. | ......... | 242/608.1 |
| 6,435,450 B1 * | 8/2002 | Shields et al. | ............ | 242/594.3 |
| 2004/0232273 A1 * | 11/2004 | Arai et al. | .................... | 242/603 |
| 2004/0245362 A1 * | 12/2004 | Ast et al. | ................. | 242/388.6 |

FOREIGN PATENT DOCUMENTS

| | | |
|---|---|---|
| DE | 10 60 279 B | 6/1959 |
| DE | 70 30 622 U | 11/1970 |
| DE | 70 31 318 U | 1/1971 |
| DE | 4018440 A1 | 12/1991 |
| DE | 40 26 782 A1 | 3/1992 |
| DE | 199 28 731 A1 | 1/2001 |
| JP | 59-149276 | 8/1984 |

* cited by examiner

*Primary Examiner*—John Q Nguyen
*Assistant Examiner*—Stefan Kruer
(74) *Attorney, Agent, or Firm*—Martin Fleit; Paul D. Bianco; Fleit Gibbons Gutman Bongini & Bianco PL

(57) ABSTRACT

The invention provides a rotation transformer for a cable connection including separation discs rotatable about a longitudinal axis. In use, one end of a cable executes a limited number of revolutions about the longitudinal axis in relation to the other end while maintaining an uninterrupted connection between the two ends. The distance between the rotatable separation discs is measured such that a maximum of two coils of the cable lie on one plane between two separation discs. The cable is guided through the discs without converging and is wound alternately from the outer diameter of a disc to the longitudinal axis and vice versa between the pairs of separation discs.

3 Claims, 3 Drawing Sheets

ROTATION TRANSFORMER FOR CABLE CONNECTIONS

FIELD OF THE INVENTION

The invention relates to a rotation transformer for a cable connection.

BACKGROUND OF THE INVENTION

In the sense of this description and the claims, a cable is understood to be any elongated, flexible, or elastic material for the transport of energy, information, or materials, in particular, but not exclusively, an electrical cable, an optical cable (including, for example, optical fibers), a delivery pipe, etc.

A solution is known from JP 59.149276 in which the cable is mounted on an elastic flat spiral spring and can be rotated with the axial spring end. Disadvantages of this solution include, first, its large diameter and, second, the rather large restoring moment of the rotating part in the limiting positions and changing with the rotations.

A solution is known from DE 402 6782 in which a helical carrier body has all inflection point and the cable is embedded and in this way guided with a force fit in the carrier body.

From DE 199 28 731 C2, a device for winding, unwinding, and storing elongated, flexible parts is known, which is not formed, however, as a rotation transformer. This device is used for the purpose of holding a cable, like in a cable drum, wherein this cable can be removed from the drum by pulling on the two cable ends. Here, the cable has no guidance by a bearing axis, however, and due to the only two spaces between adjacent separation discs, a controlled winding and unwinding, like that required for a precise rotation transformer, is not possible.

DE 703 0 622 and DE 703 1 318 disclose a device for winding electrical measurement cables and a cable and hose box as their respectively subject matters. In both publications, however, the problem of rotation transmission is not addressed in any way; instead both publications are concerned only with the storage and release of cables, and the problem of rotating the cable ends relative to each other plays no role.

Finally, DE 40 18 440 A1 shows a spiral line arrangement which is connected on one end to a device that can rotate back and forth about a rotational axis, and on the other end to a stationary device, and which can rotate in or out with the rotation of the rotatable device. The solution proposed is technically exceedingly complicated, because a synchronizing drive for the individual cascade arrangements is necessary.

Therefore, there is the task of constructing a rotation transformer for a cable connection that can be produced simply and cost-effectively, generates no restoring moments, requires no special drive, and places no special requirements on the cable configuration or embedding.

SUMMARY OF THE INVENTION

This task is achieved with the characterizing features of the independent claims. Advantageous configurations follow from the subordinate claims.

BRIEF DESCRIPTION OF THE DRAWINGS

One embodiment of the invention is explained in more detail below with reference to the individual drawings. Shown herein are the following views.

DETAILED DESCRIPTION OF THE INVENTION

Figure 3:
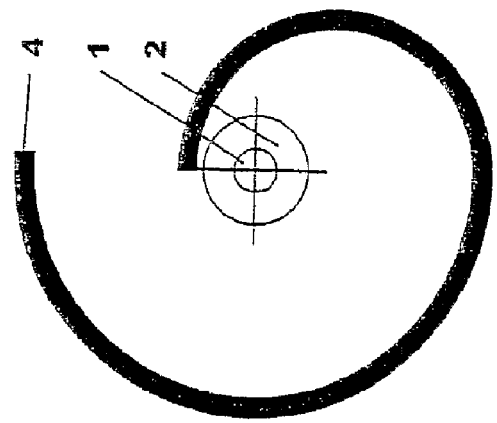
FIG. 3 is a top view of a second cable winding of the rotation transformer shown in FIG. 1 that is adjacent to the first cable winding and taken along line III-III in FIG. 1.
Figure 2:
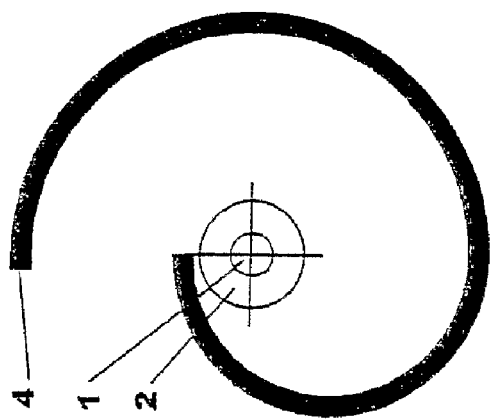
FIG. 2 is a top view of a first cable winding of the rotation transformer shown in FIG. 1 between a pair of separation discs and taken along line II-II in FIG. 1.
Figure 1:
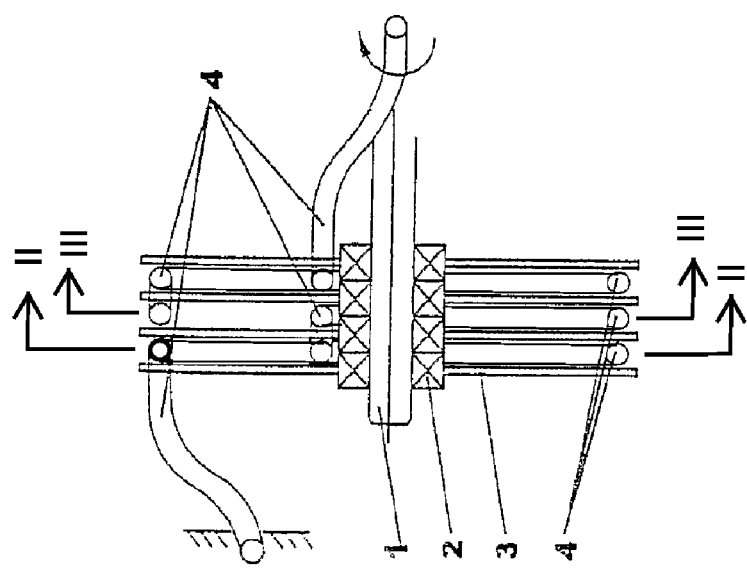
FIG. 1 is a partial side sectional view of a rotation transformer according to the invention wherein a cable winding between each pair of adjacent separation discs is shown having been wound once around an axis, the section is taken through the axis of the rotational transformer, the contact lugs and the cable lugs are omitted for clarity.
Figure 6:
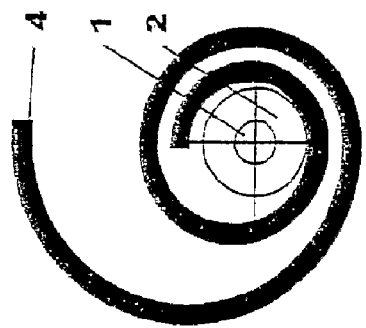
FIG. 6 is a top sectional view of the second cable winding of the rotational transformer shown in FIG. 3, wherein the separation discs were rotated by one more rotation into the position shown in FIG. 4, the section is taken along line VI-VI in FIG. 4.
Figure 5:
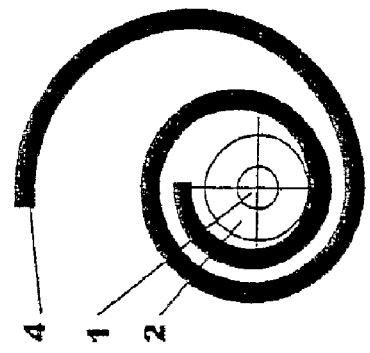
FIG. 5 is a top sectional view of the first cable winding of the rotational transformer shown in FIG. 2 wherein the separation discs were rotated by one more rotation into the position shown in FIG. 4 the section is taken along line V-V in FIG. 4.
Figure 4:
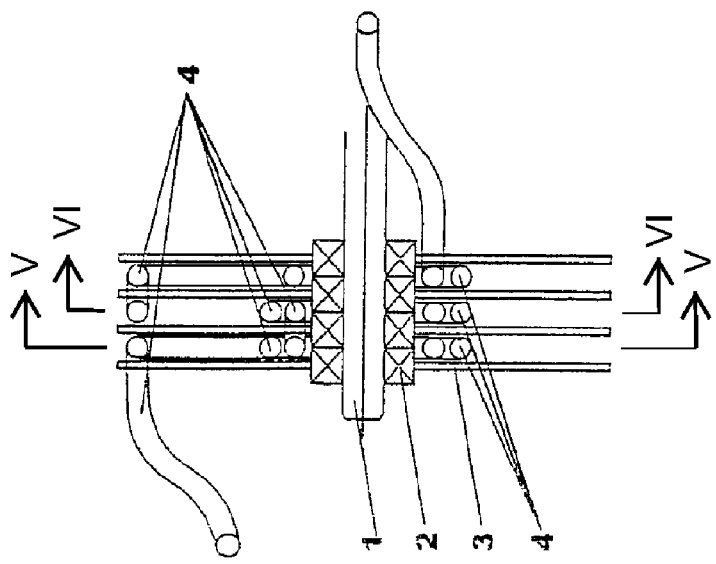
FIG. 4 is a side sectional view of the rotation transformer shown in FIG. 1 wherein a cable winding between each pair of adjacent separation discs is shown having been wound twice around the axis because, wherein each separation disc was rotated by one more rotation relative to FIG. 1, the contact lugs and the cable lugs are omitted for clarity.

FIG. 1 shows a longitudinal axis 1, about which the entire arrangement can rotate. On the axis 1 sit bearings 2, wherein each bearing 2 carries a separation disc 3, preferably made from metal or plastic, and the separation discs 3 can rotate about the bearing axis 1 independently of each other on the bearings 2 by means of the individual bearing arrangement. The distance of the separation discs 3 is dimensioned so that the cable 4 lying between these discs has slight lateral play and so that it can move between the separation discs 3 without additional means and is not clamped tightly by these discs, but is prevented from forming several layers one next to the other and also there is no significant lateral slippage of successive windings. The separation discs 3 have openings 7 and 8, which are shown in detail in FIG. 7 and by means of which the cable 4 can pass into the spaces between adjacent separation discs. An opening 7 and an opening 8 are formed in the separation discs 3 approximate a respective inner diameter and outer diameter of the separation discs and the cable 4 is fed into a space between two separation discs, so that it runs in a spiral shape from the inner diameter to the outer diameter, as shown in FIG. 2. Then it enters through the opening in the separation disc 3 from the outer diameter into the space on each side of this separation disc 3 and in turn runs from the outer diameter to the inner diameter in a spiral shape. This alternating of the winding course is performed through all of the separation disc spaces. Through this cable guidance, cable convergence within an intermediate space between adjacent separation discs 3 is prevented. The cable length of the binding winding of the cable 4 shown in FIGS. 2 and 3 is dimensioned so that for a rotation of the cable feed, just one more winding is allowed into the next intermediate space relative to the cable lead-out for each intermediate space. This state is shown in the otherwise equal FIGS. 4, 5, and 6. Here each separation disc 3 has been rotated by one more rotation relative to the previous disc.

Figure 8:
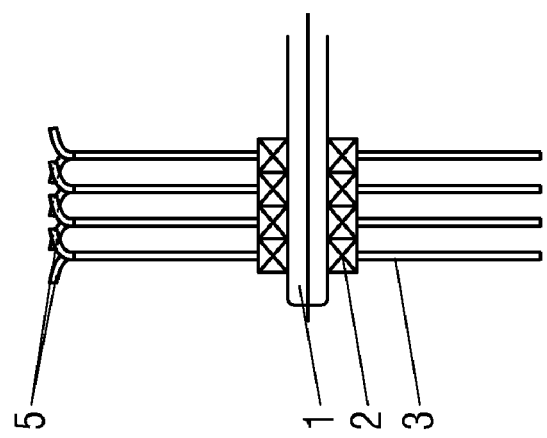
FIG. 8 is a side sectional view taken through the axis of the rotation transformer shown in FIG. 7, for clarity the cable and the cable lugs are omitted.
Figure 7:
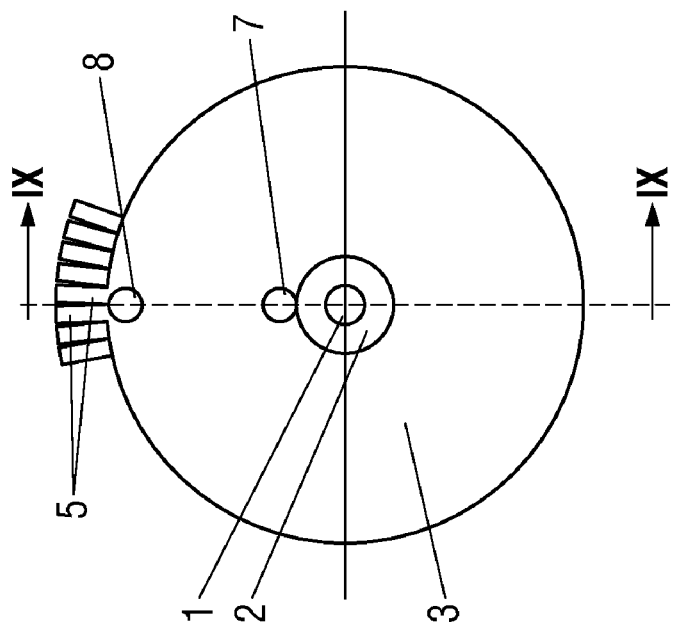
FIG. 7 is a top view of a rotation transformer with openings formed therein and contact lugs disposed on the separation disc, the cable lugs are omitted for clarity.

So that this one additional rotation can be realized precisely and so that the cable 4 is not too greatly tensioned, the separation discs 3 each have on the outer periphery two contact lugs 5, as shown in FIG. 7, which are bent in alternate axial directions according to FIG. 8. In this way, the contact lugs 5 of each separation disc 3 allow precisely one rotation of movement freedom relative to the adjacent separation disc 3.

Because approximately one rotation is allowed by each individual separation disc 3, the total number of rotations between the cable lead-in and lead-out of the rotation transformer according to the invention is equal to the number of separation discs 3 (without consideration of the housing limits).

In another not-shown variant, the cable 4 is arranged between the separation discs 3 such that in the wound state, three or more windings are produced. The relative rotation between the adjacent separation discs is then limited by an elastic sliding pad and a spiral guide path with corresponding rotation angle.

Figure 9:
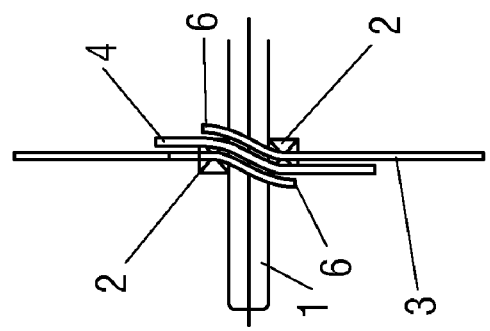
FIG. 9 is a partial, diagrammatic side sectional view of the rotation transformer shown in FIG. 1 having cable lugs to guide a cable through an opening in a separation disc, the section being taken along line IX-IX in FIG. 7, the contact lugs are omitted for clarity.

As mentioned above, FIG. 9 shows how the cable 4 is fixed in the separation discs 3 by means of guide lugs 6 and is held in the axial movement, so that the free length between the separation discs 3 remains constant, without bending of the cable.

The invention claimed is:

1. A rotation transformer for a cable connection comprising a longitudinal axis (1) and separation discs (3) having respective contact lugs (5) on an outer periphery wherein one end of a cable (4) is capable of executing a limited number of revolutions about the longitudinal axis (1) relative to its other end while maintaining an uninterrupted connection between the two ends, wherein each of the separation discs (3) is individually rotatable on the longitudinal axis (1) and the respective contact lugs (5) are structured to contact one or more adjacent lugs to limit a maximum angle of rotation between two adjacent discs (3) relative to one another, wherein a distance between two of the discs (3) allows a maximum of two turns of the cable (4) in one plane, and wherein the cable (4) is guided by a bearing arrangement on the transformer without crossing and wound between discs alternating from an outside diameter of a disc (3) to the longitudinal axis (1) and conversely from the longitudinal axis (1) to the outside diameter.

2. The rotation transformer according to claim 1, wherein a number of revolutions of the ends of the cable (4) are determined by the number of separation discs (3) and windings stored there.

3. The rotation transformer according to claim 1, wherein the separation discs (3) have openings including guide lugs (6) which secure cable (4) so that its free length between two adjacent discs (3) cannot change and so that it cannot be damaged or impaired by excessive pressure.

* * * * *